(12) United States Patent
Gatlin et al.

(10) Patent No.: US 8,993,492 B2
(45) Date of Patent: Mar. 31, 2015

(54) CROSSLINKING COMPOSITION FOR HYDROCARBON GELS

(75) Inventors: Larry W. Gatlin, San Antonio, TX (US); Glen E. Walden, The Woodlands, TX (US); Ernest McMillan, Kingwood, TX (US)

(73) Assignee: CST Performance Products Corp., Conroe, TX (US)

( * ) Notice: Subject to any disclaimer, the term of this patent is extended or adjusted under 35 U.S.C. 154(b) by 374 days.

(21) Appl. No.: 13/585,220

(22) Filed: Aug. 14, 2012

(65) Prior Publication Data

US 2014/0051611 A1 Feb. 20, 2014

(51) Int. Cl.
| | | |
|---|---|---|
| *C09K 8/62* | (2006.01) | |
| *C07F 9/08* | (2006.01) | |
| *C09K 8/64* | (2006.01) | |
| *C09K 8/68* | (2006.01) | |
| *C09K 8/82* | (2006.01) | |
| *C10L 7/02* | (2006.01) | |

(52) U.S. Cl.
CPC ... *C07F 9/08* (2013.01); *C09K 8/64* (2013.01); *C09K 8/685* (2013.01); *C09K 8/82* (2013.01); *C10L 7/02* (2013.01)
USPC ........................................................ 507/226

(58) Field of Classification Search
CPC ......... E21B 43/12; E21B 47/00; E21B 47/06; E21B 34/08; E21B 43/16; E21B 43/24; E21B 43/26; E21B 43/267; E21B 44/00; E21B 10/02; E21B 10/55; E21B 17/00; E21B 2033/005; E21B 21/00; E21B 23/01; E21B 17/023; E21B 17/042; E21B 17/08; E21B 17/1064; E21B 17/1078; E21B 17/20; E21B 19/00; E21B 19/06; E21B 19/14; E21B 19/16; E21B 19/166; E21B 2010/563; E21B 2023/008; E21B 2034/002; C09K 3/00; C09K 3/30; C09K 5/045; C09K 8/36; C09K 8/52; C09K 8/62; C09K 8/68; C09K 8/80; C09K 21/08; C09K 2205/10; C09K 2205/24; C09K 2205/32; C09K 2208/30; C09K 5/00; C09K 8/18

See application file for complete search history.

(56) References Cited

U.S. PATENT DOCUMENTS

| | | | | |
|---|---|---|---|---|
| 5,647,900 A | * | 7/1997 | Smith et al. .................... | 106/285 |
| 6,149,693 A | * | 11/2000 | Geib ................................ | 44/270 |
| 2012/0000660 A1 | * | 1/2012 | Gatlin et al. ................ | 166/308.1 |
| 2012/0000661 A1 | * | 1/2012 | Gatlin et al. ................ | 166/308.1 |

* cited by examiner

*Primary Examiner* — Susannah Chung
*Assistant Examiner* — Kumar R Bhushan
(74) *Attorney, Agent, or Firm* — Beck & Thomas, P.C.

(57) ABSTRACT

A crosslinking composition for hydrocarbon gels containing phosphate ester gelling agents comprising a modified imidazoline or pyrimidine including an alkyl group (or unsaturated carbon chain) or of 10 to 22 carbon atoms, a polyamine, and ferric sulfate. The method of making the crosslinking agent features adding the polyamine after reaction of the other ingredients; unique gels formed with the crosslinking agent are particularly effective for LNG at very cold temperatures.

14 Claims, No Drawings

CROSSLINKING COMPOSITION FOR HYDROCARBON GELS

TECHNICAL FIELD

Crosslinking compositions for creating gels, and related methods, are useful in formation fracturing for recovering hydrocarbons from the earth. The crosslinkers, which generate gels together with orthophosphate esters, include novel combinations of certain imidazolines and polyamines as well as iron compounds.

BACKGROUND OF THE INVENTION

Gelled fluids have been used for pipeline cleaning, well stimulation, and for cleaning well bores, but the most common and economically important use for gelled fluids in hydrocarbon recovery is in formation fracturing, which is well known. See, for example, Smith et al U.S. Pat. No. 5,417,287, McCabe et at U.S. Pat. No. 5,514,645, Graham et al U.S. Pat. Nos. 6,004,908 and 6,147,034, and Taylor et at U.S. Pat. Nos. 6,511,944, 6,544,934, and 7,341,103. The gelled liquid is sent down the well under great pressure and through perforations in the well casing, where it causes fractures in the earth formation. The gelled fluid is used to suspend and transport a hard granular material such as sand, known as a "proppant" for its function of maintaining the openings of the fissures so the recovered oil or gas can be drawn from the formation into the recovery system.

Phosphate esters are widely used in the hydrocarbon recovery industry to form the basis of the gel, after crosslinking by injecting sources of iron or aluminum, as is known in the art.

Partially because of the stresses on the gel from being forced through the well casing perforations and from flowing under pressure in contact with the irregular surfaces in the formation fractures, it has been difficult for workers in the art to assure adequate stability of the gel when it finally reaches the smaller fissures and interstices in the formation comprising the ultimate destination of the proppant. Whether it is in an aqueous or a hydrocarbon base, the gel is vulnerable to degradation from the stress of such surface contact and turbulence-inducing pathways under great pressure; the turbulent proppant itself also exerts physical stress on the molecular structure of the gel. There is a need in the art for more stable gels, and particularly for stable crosslinkers that form the gels, yet the gels must also be readily pumpable and susceptible to breaking when it is necessary to assure the flow of hydrocarbons from the fractured formation. In addition to these basic performance criteria, there is an increasing need for hydrocarbon gels having a demonstrable ability to carry sand and other proppants at very cold temperatures.

SUMMARY OF THE INVENTION

We have invented a versatile crosslinker for hydrocarbon gels which imparts improved stability and performance at very cold temperatures.

The invention includes a unique combination of a substituted imidazoline or pyrimidine, coconut oil (or other oil-derived) diethanolamide, a source of iron, and a polyamine. The crosslinker is especially effective for cold gel applications, such as with liquefied propane and liquefied natural gas. References herein to LNG are meant to mean liquefied natural gas, liquid propane, and other low molecular weight hydrocarbon liquids, compressed or not, used in fracturing formations, particularly in very cold temperatures.

DETAILED DESCRIPTION OF THE INVENTION

Our crosslinking formulation is especially effective in LNG gels at temperatures of −18° C. or lower, but will perform well in any hydrocarbon base. The LNG or other hydrocarbon base will contain a phosphate ester gelling agent in an amount from 1 L/m$^3$ to 20 L/m$^3$. By a "phosphate ester gelling agent," we mean, in general, that phosphated alcohols, alcohol oxyalcoholates, aryl hydroxyl or aryl hydroxyalcohols may be used as the phosphorous-containing portion of the gel former; they may be phosphated with $P_2O_5$, $PCl_3$, $POCl_5$, or polyphosphoric acid. More specifically, an orthophosphate diester of the formula $HPO_4RR'$ where R is a straight or branched chain alkyl, aryl, alkoxy, or alkaryl group having about 6 to about 18 carbon atoms and R' is hydrogen or an aryl, alkaryl, alkoxy, or alkyl group having up to about 18 carbon atoms may be used as the phosphorous-containing material. We can also use a product of the reaction of orthophosphoric acid ($PO_4$) with an excess of a mixture of $C_2$ to $C_6$ alcohols to maximize the formation of diesters. Any other phosphate or phosphonate gel-former for hydrocarbons described or used in the prior art can also work with our novel crosslinker; these are included in our definition of a phosphate ester gelling agent for our purposes.

An effective composition of our invention can be made according to the following recipe, using the proportions (by weight) of ingredients described in Table I:

TABLE I

| | Component | Weight Percent |
|---|---|---|
| 1 | Glycol ether EB | 14.95 |
| 2 | Polyfac T-653 | 9.45 |
| 3 | 7903 (Amide of DMAPA) | 4.05 |
| 4 | 78091 (Amide of DEA) | 1.80 |
| 5 | Stepantan AS-12 46 | 4.50 |
| 6 | Glycerin, refined | 4.50 |
| 7 | Ferric Sulfate, 60% | 60.75 |
| | | 100.00 |
| 8. | DMAPA or a related polyamine - an additional 0.1-4.0% | |

1. Glycol ether EB is a brand name of Lyonellbasell for ethylene glycol 2-butane ethanol, or ethylene glycol monobutyl ether, $CH_3CH_2CH_2CH_2OCH_2CH_2OH$.
2. Polyfac T-653 is an imidazoline made by reacting diethylene triamine with tall oil.
3. 7903 is the reaction product of 74.33 weight percent degummed soybean oil and 25.67 weight percent dimethyl aminopropylamine (DMAPA).
4. 78091 is a diethanolamide, made by reacting coconut oil with diethanolamine
5. Stepantan AS-12 46 is sodium dodecene sulfonate in 40-60% water. The amount of water included with the sodium dodecene sulfonate may vary somewhat, but excess water is not recommended.
7. Ferric sulfate, 60% includes 40% water, which is near saturation. A small amount of additional water may be tolerated, but is not recommended.

The first six listed components are charged to a vessel and mixed for thirty to sixty (30-60) minutes. There is a slight exotherm to about 100-110° F.; a chilling mass is applied to reduce and maintain the temperature at 80-90° F. After the 30 to 60 minutes of mixing, a quantity of DMAPA or a related polyamine (see below) is then added and mixed into the composition for thirty to sixty (30-60) minutes. More exotherm is seen to 110-125° F.; the chiller is applied for an endotherm down to 75-90° F. The ferric sulfate is then charged to the vessel and mixed for thirty to sixty (30-60) minutes. The amounts of the above listed components may be varied ±10%; if one or more components is varied within this range, others should be adjusted, if necessary, to achieve 100% for the total of listed components 1-7 without any individual component having varied more than 10% more or less by weight. It should be noted that the glycerine does not enter into a reaction; accordingly the term "reaction product"

as used herein means the reaction product of the ingredients with or without glycerine; likewise, while the sodium dodecene sulfonate plays a role in the reaction, we do not believe it is transformed chemically to a significant extent by reaction with the other components, and, again, the term "reaction product" as used herein means the reaction product of the ingredients with or without sodium dodecene sulfonate.

As indicated in the Summary of the Invention, one of the ingredients, #8, of our invention is a polyamine. For the sake of brevity, it is called DMAPA, which means dimethylaminopropylamine. Although this particular compound, $(CH_3)_2NCH_2CH_2CH_2NH_2$, is used to make the component designated as amide 7903, we also use DMAPA or a related polyamine as an additive to the reaction mixture after about 30 minutes of mixing the first six listed ingredients. We may use for this after-addition any polyamine of the formula

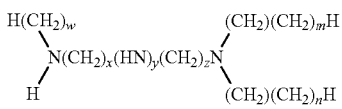

[Polyamine A]

where w is a number from 0-15, x is a number from 2-8, y is 0 or 1, z is a number from 0 to 8, and m and n are independently selected numbers from 0 to 15. In addition to DMAPA, other examples within the general formula of Polyamine A include dimethylaminoethylamine $(CH_3)_2NCH_2CH_2NH_2$ and didecylaminohexylamine $H_2N(CH_2)_6N[(CH_2)_{12}H]_2$. The amount of polyamine to be added may vary from 0.1% to 4.0% by weight of the other seven ingredients. Typically, mixing into the batch will require about ten minutes. The composition after adding and mixing Polyamine A is a good representation of our crosslinking agent. It should be understood that the mixing times stated in this and the previous paragraph are not critical; they are related to the vagaries of the temperature and vigor of mixing, the objective being to accomplish a good mix.

The imidazoline (component 2) may be within the general formula

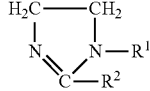

[Imidazoline B]

where $R^1$ is an amino alkyl group containing 2 to 6 carbon atoms and $R^2$ is an alkyl group (or unsaturated carbon chain) or of 10 to 22 carbon atoms. As described in U.S. Pat. Nos. 2,468,163, 7,857,871, 4,722,805, 3,846,071, 2,598,213, 3,514,399 and elsewhere in the patent and other literature, it is known to make compounds of the above formula "Imidazoline B" by reacting a carboxylic acid, or fatty acid, (from which $R^2$ is derived) with an ethylene polyamine in which one of the amine groups is a primary amine and another is a secondary amine; if a third amine nitrogen is a tertiary amine, it will not enter into the ring formation but will be found in the $R^1$ group. Where $R^1$ includes a primary amine group, the reactant may have been diethylene triamine (sometimes known as DETA), yielding an $R^1$ radical of the formula —$CH_2CH_2NH_2$. Persons skilled in the art will note that our component number 2 of Table I is made from DETA and tall oil, and in this case we describe the $R^2$ group of Imidazoline B as having been made with tall oil. Thus our imidazoline component may be made with oils and/or fatty acids of different molecular length, i.e. providing a residual carbon chain of 12-22 carbons, or a mixture of compounds containing such chains as $R^2$. Common $R^2$ chains may be saturated C12 (as from coconut), saturated C14, saturated C16, both saturated and unsaturated C18, and residuals of rosin acid, which is found in tall oil. Other amine reactants for making the imidazoline include triethylene tetramine (TETA), and triethylene propylamine (TEPA). Common $R^1$ groups are C2, C4, and C6. Where a propylene group appears next to the primary amine, a six-membered pyrimidine ring will be formed, having three carbons between the nitrogens, otherwise similar to imidazoline, and such a pyrimidine is also contemplated within our invention. Thus this component can be a pyrimidine having substituents $R^1$ and $R^2$ as described above.

In addition to the above stated quantity variations of plus or minus 10% of the specific listed ingredients, and variations within the general formulas provided above, it should be understood that our invention may include variations in the compositions of other individual components, namely:

Glycol ether EB may be replaced by a compound within the general formula $R^3$—O—[$R^4$—O—]$_{1-2}$H where $R^3$ is a linear or branched alkyl group of 3-6 carbon atoms and each $R^4$ is independently a linear or branched alkyl group of 2-6. Examples are ethylene glycol 2-propane ethanol, ethylene glycol 2-pentane ethanol, propylene glycol tertiary butyl ether, and dipropylene glycol n-butyl ether.

7903: Cottonseed oil may replace soya oil. The reaction product is typically dialkylaminopropyl amide or higher up to dialkylamino hexyl amide or higher. The exact ratio of 74.33 to 25.67 is not essential—it may be varied between 60:40 and 80:20; a slight excess of either reactant will not have a noticeably undesirable result in our invention.

In 78091, the coconut oil may be replaced by other animal or vegetable oils, preferably also having a high percentage of saturated fatty acids, such as palm kernel oil.

Our crosslinnker formulation may therefore comprise any combination of components within the following guidelines, in parts by weight:

TABLE IA

| | |
|---|---|
| 1. A compound of the formula $R^3$-O[$R^4$-O]$_{1-2}$H where $R^3$ is a linear or branched alkyl group of 3-6 carbon atoms and each $R^4$ is independently a linear or branched alkyl group of 2-6 carbon atoms | 13-17 |
| 2. Imidazoline B or a pyrimidine having similar substituent groups | 8.5-10.5 |
| 3. An amide made by reacting a vegetable oil and a polyamine of the formula Polyamine A | 3.6-4.5 |
| 4. A vegetable oil diethanolamide | 1.6-2.0 |
| 5. Sodium dodecene sulfonate in 40-60% water | 4.0-5.0 |
| 6. Glycerin | 4.0-5.0 |
| 7. Ferric sulfate, 40%-80% active | 54-67 |
| 8. Polyamine A | 0.1-4 |

Tests were conducted on variations of our crosslinking formulations, using a readily available commercial phosphate gelling agent. In Table II, results are shown for gel tests employing a standard Hamilton Beach mixer at a controlled moderate speed. Liquid pentane or propane is the base. The test is conducted at room temperature or minus 20° C. to minus 28° C. [−20° C. to −28° C.]; the temperature will drop somewhat because of the temperature of the liquid base; this is not measured. The timer is started immediately on addition of the last ingredient, and the mix will be expected immediately to exhibit a vortex. As the viscosity continues to build, the vortex will recede. When a vortex is no longer visible, the time, in minutes, is recorded as "closure," noted as "V." Mixing continues, and the fluid builds a slight mound, called the "crown," the time, in minutes, for which is recorded as "C." Sometimes in the very cold conditions the crown will occur before the closure. In Table II, the first units under "sand" represent the number of seconds noted for the beginning of the suspension of sand; the second time is the number of seconds required for full suspension of the sand.

TABLE II

| Formula | Room temperature | | | | Frozen (−20 C.) | | | | Pour Point | Sand −20 C. |
|---|---|---|---|---|---|---|---|---|---|---|
| | V | C | Gel | Lip | V | C | Gel | Lip | | |
| A | 1 | 3 | SB, kerplunk[1] | 21 | 54 | 1:55 | Blob[2] | 3:00 | Slow | 35-45 |
| B | 1 | 3 | Blob | 43 | 56 | 1:54 | Blob | 3:10 | Pass | 20-48 |
| C | 1 | 4 | Blob | 58 | — | — | — | — | — | — |
| D | 1 | 4 | Blob | 1:06 | 49 | 3:10 | Blob | 4:45 | Pass | 20-30 |
| E | 1 | 3 | Blob | 32 | — | — | Blob | — | — | 30-40 |
| F | 2 | 4 | SB, kerplunk | 32 | 56 | 2:04 | Blob | 3:41 | — | — |
| G | 1 | 3 | Blob | No | No | 3:13 | Poured | 5:26 | Pass | 30-50 |
| H | 1 | 5 | Blob | No | 25 | 1:50 | Blob | 4:05 | Pass | 40-55 |
| I | 1 | 5 | Blob | 1:30 | No | 2:44 | Blob | 4:56 | Pass | 40-60 |
| J | 1 | 3 | Blob | 30 | 1:21 | 2:38 | Blob | 4:00 | Pass | 20-35 |
| K | 1 | 2 | Blob | 2;38 | 54 | 2:40 | Blob | 4:22 | Pass | 25-40 |
| L | 1 | 4 | SB, kerplunk | 26 | 50 | 2:26 | Blob | 3:30 | Pass | 25-45 |
| M* | 1 | 5 | <Blob[3] | No | 40 | 2:18 | Blob | 4:00 | Pass | 30-55 |
| N | 1 | 4 | Blob | 50 | 1:04 | 2:30 | Blob | 4:00 | Pass | 30-45 |
| O | 1 | 4 | Blob | 1:22 | No | 1:56 | Blob | 3:15 | Pass | 45-50 |
| P | 1 | 4 | Blob | 1:30 | 30 | 2:10 | Blob | 3:40 | Pass | 40-60 |

[1] "SB" means a superblob - a rigid gel which flows, but is not considered moldable or inflexible. It flows and retains itself without breaking or shattering. "Kerplunk" defines the most rigid gel, not able to run or flow except as a whole. "Kerplunk" is almost set to glaze, or solid or immobile, but pumpable.
[2] "Blob" means a semirigid gel which flows easily and then sets, becoming poorly mobile on standing.
[3] "<Blob" - flows easily but sets up more slowly than blob.
All observations in Table II, including the timing of lip formation, are somewhat subjective but are/were performed by the same lab worker.

*Formula M is the composition of Table I. In the other formulations A-L and N-P, concentrations of the glycol ether EB, glycerin, and ferric sulfate were the same as formula M, while the other components were varied somewhat. Sand suspension at low temperatures was considered important, but also the formulation must be able to perform under a wide variety of conditions, and all of these are more or less subjectively considered in selecting the preferred composition. The tests represented in Table II were selected from a much larger series of similar tests on various different formulations whose results were not considered to be as good. Formula M's performance was excellent at both room temperature and −20° C. and as low as (−)28° C.

The composition of Table I was also tested in a loop reactor with liquid propane and was found able to provide good gels over a wide range of temperatures.

Therefore, it is to be understood that our invention comprises a crosslinking composition for making gels in hydrocarbons comprising the reaction product of, in parts by weight ("p/w"):

(a) 13-17 p/w of a compound of the formula $R^3$—O—[ $R^4$—O$]_{1-2}$H where $R^3$ is a linear or branched alkyl group of 3-6 carbon atoms and each $R^4$ is independently a linear or branched alkyl group of 2-6 carbon atoms, or a mixture of such compounds, (b) 8.5-10.5 p/w of an imidazoline or pyrimidine of the formula

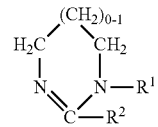

where $R^1$ is an amino alkyl group containing 2 to 6 carbon atoms and $R^2$ is an alkyl group (or unsaturated carbon chain) or of 10 to 22 carbon atoms.

(c) 3.6-4.5 p/w of an amide or mixture of amides made by reacting a vegetable oil and a polyamine of the formula

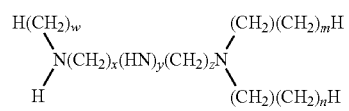

where w is a number from 0-15, x is a number from 2-8, y is 0 or 1, z is a number from 0 to 8, and m and n are independently selected numbers from 0 to 15, (d) 1.6-2.0 p/w of a vegetable oil diethanolamide,
(e) 0-5.0 p/w sodium dodecene sulfonate in 40-60% water,
(f) 0-5.0 p/w glycerin,
(g) 54-67 p/w ferric sulfate, 40-80% in water, and
(h) 0.1-4 p/w polyamine of the formula

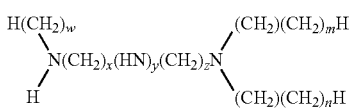

where w is a number from 0-15, x is a number from 2-8, y is 0 or 1, z is a number from 0 to 8, and m and n are independently selected numbers from 0 to 15, said crosslinking composition being effective to form a gel in with a phosphate ester gelling agent in LNG at a temperature of from −20° C. to −28° C.

Our invention also includes a method of making a crosslinking composition for hydrocarbon gels comprising (a) mixing together (i) 13-17 parts by weight one or more compounds of the formula $R^3$—O—[$R^4$—O—]$_{1-2}$H where $R^3$ is a linear or branched alkyl group of 3-6 carbon atoms and each $R^4$ is independently a linear or branched alkyl group of 2-6 carbon atoms, or a mixture of such compounds, (ii) 8.5-10 parts by weight of an imidazoline or pyrimidine of the formula

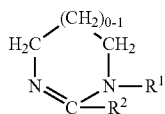

where $R^1$ is an amino alkyl group containing 2 to 6 carbon atoms and $R^2$ is an alkyl group (or unsaturated carbon chain) or of 10 to 22 carbon atoms, or a pyrimidine having similar substituent groups, (iii) 3.6-4.5 parts by weight of an amide or mixture of amides made by reacting a vegetable oil and a polyamine of the formula

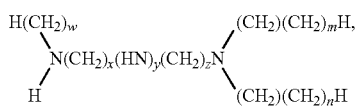

where w is a number from 0-15, x is a number from 2-8, y is 0 or 1, z is a number from 0 to 8, and m and n are independently selected numbers from 0 to 15, (iv) 1.6-2.0 parts by weight of a vegetable oil diethanolamide, (v) 4.0-5.0 parts by weight sodium dodecene sulfonate in 40-60% water, and (vi) 5.0-5.0 parts by weight glycerin, thereby causing an exotherm, (b) further mixing into said mixture 0.1-4 parts by weight of a polyamine of the formula

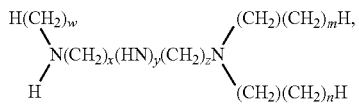

where w, x, y, z, m, and n are as indicated above, (c) mixing into said mixture 54-67 parts by weight ferric sulfate (40-80% in water), and (d) cooling said mixture throughout said mixing in steps (a), (b), and (c) to control said exotherm.

And, our invention includes a hydrocarbon gel comprising (A) a hydrocarbon base, (B), a phosphate ester gelling agent dispersed in said hydrocarbon base, and (C) a crosslinking composition for said gelling agent comprising the reaction product of (a) 13-17 parts by weight of a compound or mixture of compounds of the formula $R^3$—O—[$R^4$—O—]$_{1-2}$H where $R^3$ is a linear or branched alkyl group of 3-6 carbon atoms and each $R^4$ is independently a linear or branched alkyl group of 2-6 carbon atoms, (b) 8.5-10.5 parts by weight of an imidazoline or pyrimidine of the formula

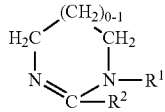

where $R^1$ is an amino alkyl group containing 2 to 6 carbon atoms and $R^2$ is an alkyl group (or unsaturated carbon chain) or of 10 to 22 carbon atoms.

(c) 3.6-4.5 parts by weight of an amide or mixture of amides made by reacting a vegetable oil and a polyamine of the formula

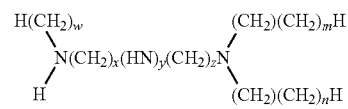

where w is a number from 0-15, x is a number from 2-8, y is 0 or 1, z is a number from 0 to 8, and m and n are independently selected numbers from 0 to 15, (d) 1.6-2.0 parts by weight of a vegetable oil diethanolamide, (e) 54-67 parts by weight ferric sulfate, 40-80% in water, and (f) 0.1-4 parts by weight polyamine of the formula

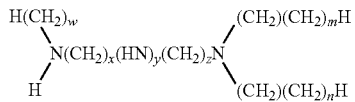

where w is a number from 0-15, x is a number from 2-8, y is 0 or 1, z is a number from 0 to 8, and m and n are independently selected numbers from 0 to 15.

The invention claimed is:

1. A crosslinking composition for making gels in hydrocarbons comprising the reaction product of, in parts by weight ("p/w"):

(a) 13-17 p/w of a compound of the formula $R^3$—O—[$R^4$—O—]$_{1-2}$H where $R^3$ is a linear or branched alkyl group of 3-6 carbon atoms and each $R^4$ is independently a linear or branched alkyl group of 2-6 carbon atoms, or a mixture of such compounds, (b) 8.5-10.5 p/w of an imidazoline or pyrimidine of the formula

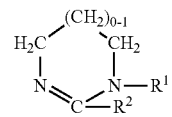

where $R^1$ is an amino alkyl group containing 2 to 6 carbon atoms and $R^2$ is an alkyl group (or unsaturated carbon chain) or of 10 to 22 carbon atoms.

(c) 3.6-4.5 p/w of an amide or mixture of amides made by reacting a vegetable oil and a polyamine of the formula

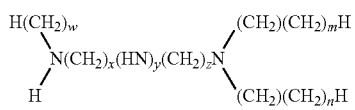

where w is a number from 0-15, x is a number from 2-8, y is 0 or 1, z is a number from 0 to 8, and m and n are independently selected numbers from 0 to 15, (d) 1.6-2.0 p/w of a vegetable oil diethanolamide, (e) 0-5.0 p/w sodium dodecene sulfonate in 40-60% water, (f) 0-5.0 p/w glycerin,
(g) 54-67 p/w ferric sulfate, 40-80% in water, and
(h) 0.1-4 p/w polyamine of the formula

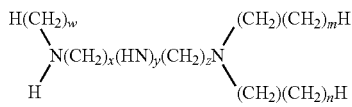

where w is a number from 0-15, x is a number from 2-8, y is 0 or 1, z is a number from 0 to 8, and m and n are independently selected numbers from 0 to 15, said crosslinking composition being effective to form a gel in with a phosphate ester gelling agent in LNG at a temperature of from −20° C. to −28° C.

2. Crosslinking composition of claim 1 wherein said polyamine (h) comprises dimethylaminopropyl amine.

3. Crosslinking composition of claim 1 wherein said imidazoline (b) comprises an imidazoline made by reacting diethylene triamine with tall oil.

4. Crosslinking composition of claim 1 wherein said amide (c) comprises an amide made by reacting soybean oil with dimethyl aminopropylamine.

5. Crosslinking composition of claim 1 wherein said diethanolamide (d) comprises a diethanolamide made by reacting coconut oil with diethanolamine.

6. Crosslinking composition of claim 1 wherein $R^1$ in said imidazoline (b) contains two amine groups.

7. Crosslinking composition of claim 1 wherein said polyamine (h) comprises didecylamionohexylamine.

8. Crosslinking composition of claim 1 wherein said compound (a) comprises ethylene glycol 2-butane ethanol.

9. Method of making a crosslinking composition for hydrocarbon gels comprising (a) mixing together (i) 13-17 parts by weight one or more compounds of the formula $R^3$—O—[ $R^4$—O ]$_{1-2}$H where $R^3$ is a linear or branched alkyl group of 3-6 carbon atoms and each $R^4$ is independently a linear or branched alkyl group of 2-6 carbon atoms, or a mixture of such compounds,
(ii) 8.5-10 parts by weight of an imidazoline or pyrimidine of the formula

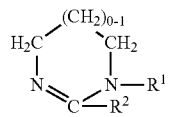

where $R^1$ is an amino alkyl group containing 2 to 6 carbon atoms and $R^2$ is an alkyl group (or unsaturated carbon chain) or of 10 to 22 carbon atoms, or a pyrimidine having similar substituent groups, (iii) 3.6-4.5 parts by weight of an amide or mixture of amides made by reacting a vegetable oil and a polyamine of the formula

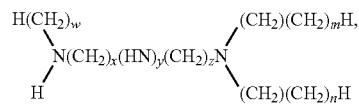

where w is a number from 0-15, x is a number from 2-8, y is 0 or 1, z is a number from 0 to 8, and m and n are independently selected numbers from 0 to 15,
(iv) 1.6-2.0 parts by weight of a vegetable oil diethanolamide, (v) 4.0-5.0 parts by weight sodium dodecene sulfonate in 40-60% water, and (vi) 5.0-5.0 parts by weight glycerin, thereby causing an exotherm, (b) further mixing into said mixture 0.1-4 parts by weight of a polyamine of the formula

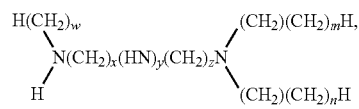

where w, x, y, z, m, and n are as indicated above, (c) mixing into said mixture 54-67 parts by weight ferric sulfate (40-80% in water), and (d) cooling said mixture throughout said mixing in steps (a), (b), and (c) to control said exotherm.

10. Method of claim 9 wherein said polyamine in step (b) comprises dimethylaminopropyl amine.

11. Method of claim 9 wherein said imidazoline in step (a) (ii) comprises an imidazoline made by reacting diethylene triamine with tall oil.

12. Method of claim 9 wherein said amide (a) (iii) comprises an amide made by reacting soybean oil with dimethyl aminopropylamine.

13. Method of claim 9 wherein said diethanolamide in step (a) (iv) comprises a diethanolamide made by reacting coconut oil with diethanolamine.

14. Method of claim 9 wherein said compound (a) (i) comprises ethylene glycol 2-butane ethanol.

* * * * *